United States Patent
Ihde

(10) Patent No.: US 8,241,037 B2
(45) Date of Patent: Aug. 14, 2012

(54) DISK IMPLANT

(75) Inventor: Stefan Ihde, Uetliburg (CH)

(73) Assignee: Biomed Est. (LI)

( * ) Notice: Subject to any disclaimer, the term of this patent is extended or adjusted under 35 U.S.C. 154(b) by 108 days.

(21) Appl. No.: 12/360,291

(22) Filed: Jan. 27, 2009

(65) Prior Publication Data

US 2010/0190139 A1     Jul. 29, 2010

(51) Int. Cl.
*A61C 8/00* (2006.01)
(52) U.S. Cl. ........................................ 433/176
(58) Field of Classification Search .......... 433/172–176; 606/70, 71, 286
See application file for complete search history.

(56) References Cited

U.S. PATENT DOCUMENTS

| | | | |
|---|---|---|---|
| 3,579,829 A * | 5/1971 | Sampson | 433/158 |
| 6,402,516 B2 | 6/2002 | Ihde | |
| 6,991,463 B2 | 1/2006 | Ihde | |
| 2003/0003419 A1* | 1/2003 | Ihde | 433/176 |
| 2005/0272007 A1 | 12/2005 | Ihde | |

FOREIGN PATENT DOCUMENTS

| | | |
|---|---|---|
| DE | 19948910 A1 | 10/1999 |
| EP | 1050282 B1 | 8/1999 |
| EP | 1336388 B1 | 12/2007 |
| FR | 2863477 | 6/2005 |
| WO | 2005/065570 A1 | 7/2005 |

* cited by examiner

*Primary Examiner* — Sunil K Singh
(74) *Attorney, Agent, or Firm* — Husch Blackwell LLP

(57) ABSTRACT

A dental implant for mounting prosthetic devices such as crowns, having a shaft having an external end adapted for receiving a prosthetic device, a foot attached to an opposing end of the shaft, the foot and shaft being generally orthogonal and the implant foot having a circular outline over an arc α with two long substantially linear sides enclosing an angle β, the linear sides being disposed substantially symmetrically with respect to the shaft.

10 Claims, 1 Drawing Sheet

DISK IMPLANT

BACKGROUND OF THE INVENTION

1. Field of the Invention

The present invention concerns a disk implant that is anchored in the jawbone by basal osseointegration and serves to accept and hold a tooth replacement or a crown.

Quite different solutions have been suggested in the past for the design and structure of the implant foot for disk implants, through which the implant is anchored in the jawbone by basal osseointegration and through which the chewing forces taken up by the implant are transferred into the jawbone.

2. Related Art

There are implants with an implant foot that is approximately square to rectangular, DE 299 17 858.7 or DE 3 018 255, and implants the foot part of which is made up of a round disk, or a multiplicity of round disks with the same or different diameters stacked vertically, as in DE 199 48 910 A1 and EP 0 935 949 B1. Implants are also known that have an implant foot comprised of two adjacent rings, EP 1 050 282 B1, and implants in which the foot part is made up of various geometric forms with different surface areas attached to each other, DE 202 02 424.5, EP 1 050 282 B1 and EP 1 336 388 B1.

SUMMARY OF THE INVENTION

The requirement for disk implants with different configurations of the implant foot necessarily arises from the various individual requirements and conditions for insertion of the implant and for assurance of a long-lasting solid seat for the inserted implant. These requirements and conditions include, for example, the individual anatomy of the jawbone, the existing bone substance, and the implant region in the patient's jaw. These and other requirements and conditions cannot be met by disk implants in which the implant foot is designed uniformly throughout.

The invention is based on the objective of providing an implant foot for a disk implant with which the greatest possible attachment of the implant foot to the corticalis of the jawbone can be attained after insertion of the implant, even with small external dimensions of the foot.

The objective is attained according to the invention by a disk implant having a shaft having an external end adapted for receiving a prosthetic device; a foot attached to an opposing end of said shaft, said foot and shaft being generally orthogonal; and said implant foot having a circular outline over an arc $\alpha$, said foot having two long substantially linear sides enclosing an angle $\beta$, said linear sides being disposed substantially symmetrically with respect to the shaft.

Advantageous further developments of the subject of the invention include: the dental implant further comprising arc $\alpha$ being between about 260° and about 280°, a throughhole in said foot, said throughhole being between said linear sides and adjacent said angle $\beta$, the angle $\beta$ being between about 35° and about 55°, said shaft having a cross section with a narrow dimension and a wide dimension, said cross section is an oval, a screw disposed to abut said angle $\beta$ of said foot such that said dental implant cannot rotate after installation, an abutment at its external end, a tip thread on said shaft.

The shaft of the implant, which has, for example, an abutment or a threaded tip, or which is designed as a cementation post, preferably has an oval or elliptical profile with the longitudinal axis of that profile lying in the direction of insertion of the implant.

To insert the implant according to the invention, a T-shaped implant bed is produced surgically in the jawbone and then the implant is inserted basally into the implant bed from the outer side of the jaw bone.

After reaching the intended final insertion position, the implant is rotated optionally to the left or right around its longitudinal axis so that one of the long sides that enclose the circular outline of the implant foot lies completely on the corticalis of the jawbone.

Because of the rotation of the implant to the left or right in the implant bed, the position of the longitudinal axis of the profile of the implant shaft changes with respect to the direction of insertion or with respect to the longitudinal axis of the vertical portion of the implant bed. Although it is hardly possible, in spite of the greatest care, to make the vertical portion of the implant bed an exact fit to the particular profile cross-section of the implant shaft, when the longitudinal sides of that profile have an oval to elliptical shape, rotation of the implant to the left or right brings them into direct contact with the walls of the vertical portion of the implant bed and holds them firmly in contact.

The outer surface of the abutment also has at least one rotational stop, which can for instance be in the form of a flat or a flat side, which interacts with a corresponding mating part in the mounting hole of an attachment and reliably prevents separate rotation of the crown or other kind of tooth replacement placed on the abutment above the attachment.

Aside from the increased contact area of the implant foot on the corticalis, which results advantageously in long-lasting secure seating of the implant and the reliable transfer of the chewing forces into the jaw bone, the solution according to the invention and the firm contact of the shaft in the vertical portion of the implant bed achieve high primary stability, as both the implant foot and the vertical part of the implant, i.e., the shaft, is in firm contact in the implant bed of the jaw bone. That was not possible with the previously known solutions for the design of the implant foot and shaft of a disk implant.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
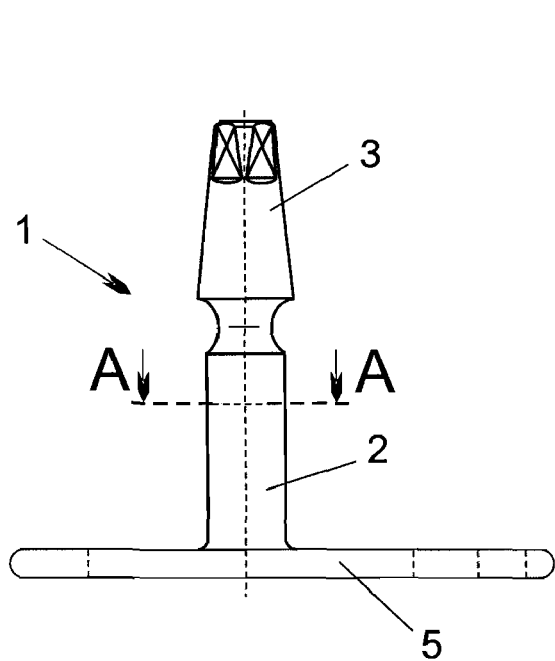
FIG. 1 is a side view of the disk implant according to the invention.

As can be seen from FIG. 1, the disk implant has a generally known design, comprising the implant foot 5 and the implant shaft 2, which is firmly connected with the implant foot 5 through the bar 4, and which is arranged orthogonally to the implant foot 5, and which has at its tip an abutment 3 to accept and fasten a crown or the attaching art of a tooth replacement.

Figure 2:
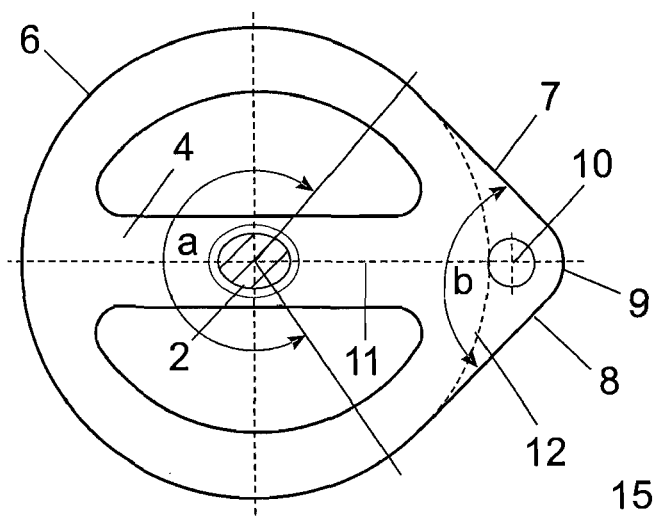
FIG. 2 is a plan view of the implant foot with the cross-section A-A shown in FIG. 1.

According to the invention, the foot section 6 of the implant foot 5 has a circular outline with a diameter approximately corresponding to the diameter of the grinding tool used to produce the implant bed 16, extending around an arc α of 260° to 280°—FIG. 2. Two long sides, 7 and 8, attach to this circular outline. They are arranged symmetrically with respect to the central axis 11 of the implant foot 5, and their ends, which extend beyond the complete circle 12 of the circular outline are connected through a radius 9 that closes off the configuration of the implant foot 5. A through-hole is provided in the end radius between the long sides 7 and 8, which enclose an angle β of approximately 35° to 55°. The through-hole serves to accept a fixing screw in case the inserted disk implant is not to be rotated in the implant bed after reaching its final insertion position. The fixing screw is screwed into the jawbone for additional fixation of the inserted implant and to secure it against any rotation—FIG. 4.

Figure 3:
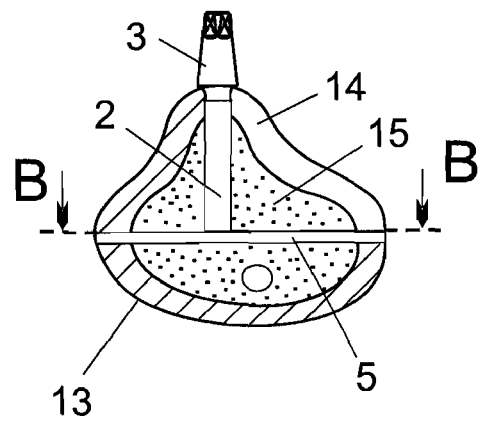
FIG. 3 is a schematic representation of the disk implant inserted into a jaw bone.
Figure 4:
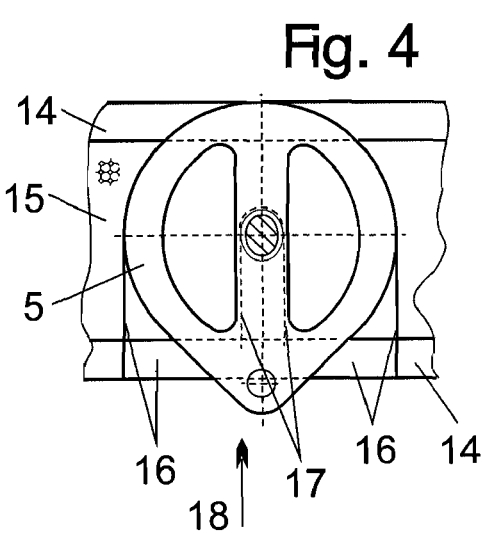
FIG. 4 is the section B-B of FIG. 3.
Figure 5:
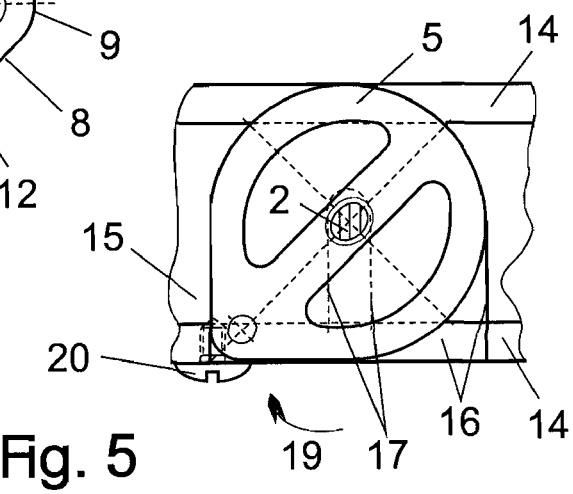
FIG. 5 is the final position of the disk implant, secured against rotation, after completion of the insertion.

FIGS. 3 to 5 show schematically the insertion of the disk implant 1 according to the invention. It is anchored in the jaw bone by basal osseointegration It is inserted in the insertion direction 18 from the outer side of the jaw bone 13 into an implant bed 16 previously prepared surgically by grinding.

In FIG. 4 the inserted disk implant 1 is in its final insertion position and is clamped in the implant bed 16 so that, due to the design according to the invention, large areas of the implant foot 5 lie against the corticalis 14 of the jawbone 13. At the same time, it is possible for the disk implant 1 to deflect to a limited amount into the spongiosa 15 of the jawbone 13, like a natural tooth, under peak loads that may occur. The basis for that is the elasticity provided in the vicinity of the implant foot 5 due to the design of the implant foot 5 and to the combination of the implant foot 5 and the implant shaft 2. If the disk implant inserted as shown in FIG. 4 is not to be rotated in the implant bed 16, it can be secured by inserting a fixing screw in the through-hole 10 in addition to its clamping into the implant bed, as previously described above.

To increase the portion of the area of the implant foot 5 that lies on the Corticalis 14 of the jaws bone 13, which can be particularly advantageous for long-lasting solid seating of disk implants with relatively small foot dimensions, the implant according to the invention can optionally be rotated by about 45° to the left or right in the implant bed 16 after reaching its final insertion position. After completion of the left or right rotation, one of the long sides 7, 8 of the implant foot 5 lies completely on the corticalis 14 of the jawbone 13, as shown in FIG. 5, thus increasing the contact area. The inserted disk implant 1, which is already clamped into the horizontal portion of the implant bed 16, can also be secured in this final position by a fixing screw 20.

According to a further feature of the invention, the implant shaft 2 preferably has an oval to elliptical profile—FIGS. 2 to 5. This measure has, for one thing, the advantage that the clear width of the vertical portion 17 of the implant bed 16 for insertion of the disk implant 1 can be ground smaller and the implant shaft 2 nevertheless has a thicker profile cross-section than an ordinary round implant shaft, so that it can accept higher forces and transfer them through the implant foot 5 into the jaw bone 13.

It is also known, from the practice of implantology, that it is hardly possible to make the vertical portion 17 of the implant bed 16 so accurately that it will stabilize the implant shaft 2, after insertion, in the vicinity of the vertical portion 17 of the implant bed 16. On rotation of the inserted implant about the longitudinal axis of the implant, in rotation direction 19, for instance, the position of the axes of the oval profile of the implant shaft 2 changes from the insertion position, in which the longitudinal axis of the oval shaft profile lies in the insertion direction 18. As the dimension of the implant shaft 2 along the longitudinal axis of the oval profile is greater than the open width of the vertical portion 17 of the implant bed 16, the longitudinal sides of the oval shaft profile come into direct contact with the side walls of the vertical portion 17 of the implant bed 16, and are forced against them on the conclusion of the rotational movement. In this way, high primary stability of the inserted disk implant is attained with relatively simple means, as both the implant foot 5 and the implant shaft 2 are solidly clamped in the implant bed 16 and in the vertical portion 17 of the implant bed 16.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A dental implant for mounting prosthetic devices such as crowns, said dental implant comprising:
   a shaft having an external end adapted for receiving a prosthetic device and said shaft having a longitudinal axis;
   a foot attached to an opposing end of said shaft, said foot and shaft being generally orthogonal;
   said implant foot having a circular outline over an arc, said foot having two long substantially linear sides enclosing an angle said circular outline and said linear sides defining a first foot width in a first direction substantially orthogonal to an said longitudinal axis of said shaft and a second foot width in a second direction substantially orthogonal to an said longitudinal axis of said shaft;
   said foot being placeable in a U shaped slot such that when one of said linear sides abuts a long side of the U shaped slot the extent of said foot along a longitudinal axis of the U shaped slot is substantially the radius of said circular outline of said foot; and
   said shaft having a cross section that defines a first shaft width in a first direction substantially orthogonal to said longitudinal axis of said shaft, and a second shaft width in a second direction substantially orthogonal to an said longitudinal axis of said shaft;
   said first foot width and said first shaft width being substantially aligned, such that when said implant is placed to abut one of said linear sides against the side of the U shaped slot, said shaft is wider with respect to the longitudinal axis of the U shaped slot than when said linear side does not abut the long side of the U shaped slot.

2. The dental implant according to claim 1 further comprising said circular outline having an arc being between about 260° and about 280°.

3. The dental implant according to claim 1 further comprising a throughhole in said foot, said throughhole being between said linear sides and adjacent said linear sides.

4. The dental implant according to claim 1 further comprising an angle between said linear sides said angle being between about 35° and about 55°.

5. The dental implant of claim 1 wherein said cross section is an oval.

6. The dental implant according to claim 1 further comprising a screw disposed to abut said angle of said foot such that said dental implant cannot rotate after installation, a shaft of said screw being substantially parallel with a plane of said foot.

7. The dental implant according to claim 1 further comprising an abutment at an external end of said shaft.

8. The dental implant according to claim 1 further comprised of a tip thread on said shaft.

9. The dental implant according to claim 1 further comprising a cementation post on said shaft.

10. The dental implant according to claim 1 further comprising an antirotation element on a surface of an abutment on said external end of said shaft.

\* \* \* \* \*